US005565984A

United States Patent [19]
Girvin

[11] Patent Number: 5,565,984
[45] Date of Patent: Oct. 15, 1996

[54] RE-ENTRANT ILLUMINATION SYSTEM FOR PARTICLE MEASURING DEVICE

[75] Inventor: Kenneth L. Girvin, Grants Pass, Oreg.

[73] Assignee: Met One, Inc., Grants Pass, Oreg.

[21] Appl. No.: 489,430

[22] Filed: Jun. 12, 1995

[51] Int. Cl.$^6$ ........................................... G01N 15/02
[52] U.S. Cl. ................................ 356/336; 356/338
[58] Field of Search .................... 356/335–343; 359/860, 863; 250/574, 573, 575, 222.2

[56] References Cited

U.S. PATENT DOCUMENTS

| | | | |
|---|---|---|---|
| Re. 33,213 | 5/1990 | Borden | 250/574 |
| 3,039,355 | 6/1962 | Suter | 88/14 |
| 3,177,760 | 4/1965 | Albert | 356/339 |
| 3,231,748 | 1/1966 | Haessler et al. | 250/218 |
| 3,457,407 | 7/1969 | Goldberg | 356/338 |
| 3,498,721 | 3/1970 | Thorndike | 356/103 |
| 3,989,381 | 11/1976 | Fulwyler | 356/338 |
| 4,387,344 | 6/1983 | Meyer | 330/4.3 |
| 4,422,761 | 12/1983 | Frommer | 356/338 |
| 4,739,177 | 4/1988 | Borden | 250/574 |
| 4,798,465 | 1/1989 | Knollenberg | 356/336 |
| 4,825,094 | 4/1989 | Borden et al. | 356/338 |
| 4,848,905 | 7/1989 | Iino | 356/338 |
| 4,893,928 | 1/1990 | Knollenberg | 356/336 |
| 5,024,526 | 6/1991 | Von Redwitz | 356/339 |
| 5,085,500 | 2/1992 | Blesener | 356/338 |
| 5,094,533 | 3/1992 | Sawada et al. | 356/338 |

Primary Examiner—Hoa Q. Pham
Attorney, Agent, or Firm—Thomas Schneck

[57] ABSTRACT

Small, mobile particles in a fluid are optically detected by an apparatus having spaced apart reflectors bordering and defining an optical cavity into which a light beam is introduced. The reflectors are arranged along axes which are slightly misaligned such that the light beam is introduced at a low angle, barely over the edge of one of the reflectors, and is repeatedly reflected between the two reflectors, overlapping itself many times in a view volume located within the optical cavity, thereby increasing the intensity of detected particles. A fluid flow is introduced into the view volume and the light scattered by particles as they pass through the intensely illuminated view volume is received by a detector which observes the view volume. The detector produces a signal which is indicative of characteristics such as the number or size of particles.

18 Claims, 4 Drawing Sheets

RE-ENTRANT ILLUMINATION SYSTEM FOR PARTICLE MEASURING DEVICE

TECHNICAL FIELD

The present invention pertains to the field of mobile particle detection. Specifically, the present invention pertains to detection of particles in fluids by means of light scattering.

BACKGROUND ART

Devices which can detect the presence of particles in fluids, including air, are well known, and are widely used in manufacturing industries. The most sensitive of these devices employ a light scattering method. As mobile particles pass through a light beam, light is scattered by the particles and received by a detector. Electronics associated with the detector then process the scattered light signal to determine factors such as the size or number of particles present.

The detection of mobile particles is especially important to semiconductor manufacturing processes which often takes place in strictly controlled environments such as "clean rooms". In such environments, mobile particles can pose a serious threat to the integrity of manufacturing processes. For example, unwanted particulate matter deposited on substrates can open or short circuits, interfere with deposition of metal films, or result in poisoned active regions. Furthermore, the fabrication precision required with increased wafer size and intricate device geometry has resulted in higher clean room standards and a need for particle detection devices to ensure protection from even smaller particles which might contaminate the production environment.

As a result of increased clean room standards and industry demands, more, lower cost laser detection devices have been introduced which can detect particles down to a fraction of a micron in size. A semiconductor laser or similar laser is commonly used to generate the laser beam in such detection devices. U.S. Pat. No. Re. 33,213 to Borden teaches the benefits of using a laser beam to generate a sheet of light in a particle detector.

Some prior art laser detection devices have placed air samples directly into the laser cavity. Such systems produce a.c. and d.c. noise due to molecular scattering. As the amount of noise increases, it becomes difficult to distinguish between the noise caused by the molecular scattering, and light scattered by mobile particles. As a result, such devices require noise reduction systems. Additionally, such prior art devices require larger lasers, and limit the user's ability to remove or change the laser.

Therefore, it is an object of this invention to provide a particle detection device with high sensitivity, but with a high signal-to-noise ratio, and a simple construction.

SUMMARY OF THE INVENTION

This object has been achieved with an optical particle detector with a sensitivity suitable for detecting particles down to one-tenth of a micron in size, while maintaining a high flow rate and a high signal-to-noise ratio using an exterior laser illumination source. This is accomplished by increasing the light intensity of an exterior laser source inside of a view volume in a novel misaligned-axes sampling cavity particle measuring and counting device.

Light intensification is achieved by repeatedly reflecting a light beam through an optical cavity having a central view volume which is bordered by opposed reflectors having optical axes which are slightly misaligned. This misalignment allows an external beam to enter the optical cavity and then folds the path of the beam with multiple overlaps as it passes through the view volume, thereby increasing light intensity. As fluid is introduced into the view volume, light scattered from mobile particles is detected and processed by a detector focused onto the view volume.

Noise associated with optical detection devices is primarily a function of the detector, not the cavity. Thus, by increasing the intensity of the signal, i.e. the incoming laser light within the view volume while keeping the number of detector cells constant, a high signal-to-noise ratio is achieved. Additionally, the size of the view volume permits flow rates which allow the detector to sample sufficient amounts of fluid.

In one embodiment, the two mirrored surfaces are spaced-apart, opposed reflectors. An incoming beam from a system of illumination optics enters the optical cavity and strikes the first reflector and is directed through the view volume towards the second reflector. The beam is then reflected by the second reflector at a slightly different angle back through the view volume towards the first reflector. The beam continues to pass between the two reflective surfaces and overlap itself in the view volume, until it falls off the edge of one of the reflectors into a light trap. As fluid flows through the intensely illuminated view volume, light scattered by particles is detected and processed by a detector focused onto the view volume.

In another arrangement, concave spherical reflectors, also having axes which are slightly misaligned, repeatedly reflect a beam of light through the view volume. In this case, the incoming beam strikes the first reflector and is focused to a spot inside the view volume. The beam then diverges and is reflected off of the second reflector back towards the view volume. However, since the two reflectors are slightly misaligned the beam is not focused in the same spot but, rather, slightly beside itself. Each time the beam bounces off of the reflectors it is focused in a slightly different position within the view volume, eventually filling it with overlapping spots. In both arrangements, the laser illumination source is separated from the view volume and the detector is within 10° of perpendicularity to the axes.

In a third embodiment, the detector is moved from the near perpendicular angle of the earlier embodiments to a low angle adjacent to the reflective axes. This embodiment is useful for measuring changes in beam intensity resembling beam extinction detectors because overall efficiency is lower in most cases, depending on the shape and dimensions of the particles and wavelength size of the beam. This design will increase the minimum sensitivity of light extinction sensors.

BEST FOR CARRYING OUT THE INVENTION

Figure 1:
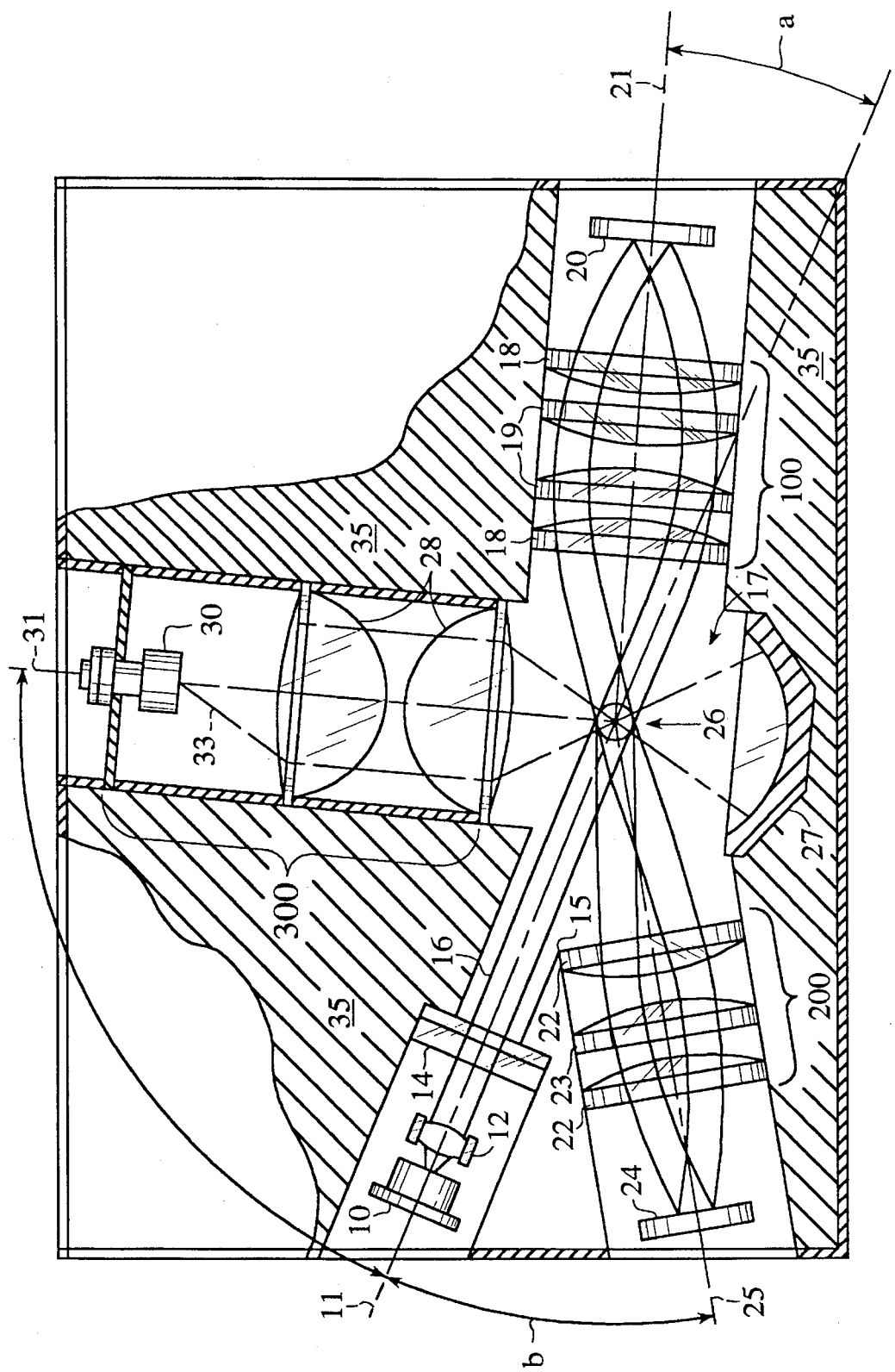
FIG. 1 is a top view of a multiply reflective particle detection apparatus in accord with the present invention.

With reference to FIG. 1, laser 10 is shown residing on laser optical axis 11. A semiconductor laser having an output power of a few milliwatts or any other laser well known in the art is suitable, so long as it is compatible with a detector used in the apparatus. As the laser 10 emits a beam, collimator 12 and cylindrical lens system 14 produce a laser beam 16 of desired width and shape.

Beam 16, having a width of a few millimeters, is projected along laser optical axis 11. In order for beam 16 to enter optical cavity 17, optical axis 25, upon which reside lens system 200 and reflector 24, must be sufficiently separated from laser optical axis 11 such that lens system 200 does not block the path of beam 16. In particular, edge 15 of the lenses in lens system 200 may be near beam 16, but should not block entry of the beam into the optical cavity. On the other hand, edges of lenses in lens system 100 intercept the beam and with mirror 20 the beam is redirected into refracting regions of lens system 200. Optical axis 25 is defined as a line running through the center region of reflector 24 coincident with the axes of symmetry of achromat 23 and meniscus lenses 22. The angle of separation B between laser optical axis 11 and left cavity optical axis 25 must be sufficiently large to permit the uninterrupted passage of beam 16 into optical cavity 17. As beam 16 enters optical cavity 17 it passes through view volume 26 and reaches lens system 100. Meniscus lenses 18 and achromats 19, which comprise lens system 100, direct beam 16 towards reflector 20 along right cavity optical axis 21. Both lens system 100 and reflector 20 are centered on optical axis 21. The optical axis 21 is a line running through the center of reflector 20 coincident with the axes of symmetry of achromats 19 and meniscus lenses 18. In order for beam 16 to be received by lens system 100, the angle of separation $\alpha$ between laser optical axis 11 and optical axis 21 must be sufficiently small such that lens system 100 remains in the path of beam 16 after several reflections from the left cavity.

Beam 16 is then reflected by reflector 20 back through lens system 100, into optical cavity 17, and through view volume 26. Beam 16 is then directed by lens system 200, containing meniscus lenses 22 and achromat 23, towards reflector 24. Reflector 24 directs beam 16 back through lens system 200 towards the view volume 26. However, optical axis 25 and optical axis 21 are slightly misaligned such that they are neither coincident or parallel. That is, the angle of separation $\beta$ between laser optical axis 11 and optical axis 25 is slightly different than the angle $\alpha$, between laser optical axis 11 and optical axis 21. This difference is less than 10° and preferably less than 5°. A typical difference between angles $\alpha$ and $\beta$ would be approximately 10°. As a result of a 10° misalignment, when beam 16 passes through view volume 26, it passes through the area at a different angle. Hence, the light energy at view volume 26 has essentially doubled. Furthermore, by increasing the intensity of the signal, laser beam 16, within view volume 26, while keeping the number of detectors constant, a high signal to noise ratio is achieved. Also, since beam 16 passes through view volume 26 at a slightly different angle, the beam spot in the view volume is elongated and the area of intense illumination within the view volume is increased. Thus a larger area is available for the introduction of a sample flow of fluid.

Beam 16 continues to be reflected between reflectors 20 and 24 at a slightly different angles until it falls off the edge of one of the reflectors where it is received by light traps 35 surrounding optical cavity 17. The difference between angles $\alpha$ and $\beta$, along with the design of lens systems 100 and 200 and reflectors 20 and 24, determines the number reflections beam 16 will make.

As fluid flows through view volume 26, a light beam ray 33 scattered by a mobile particle, not shown, will be directed by condensers 28 to detector 30. Additionally, light originally scattered away from detector 30 can be reflected by spherical reflector 27 back towards detector 30. Light traps, not shown, surrounding condensers 28 and detector 30 may be used to prevent extraneous light, scattered by particles flowing through optical cavity 17 but outside view volume 26, from being received by detector 30. Submicron particles can be detected by collection and detection system 300, having an axis which is within 20° of perpendicularity relative to optical axis 21 or axis 25.

Detector 30 is a photodetector, such as a photodiode, or CCD array, which produces an electrical signal. The electrical signal can then be conducted through a wire, not shown, attached to the detector. Well known high speed signal processing and data management electronics, not shown, can then interpret the signal derived from the scattered light allowing for determination of factors such as the size or number of particles flowing through view volume 26.

Figure 2:
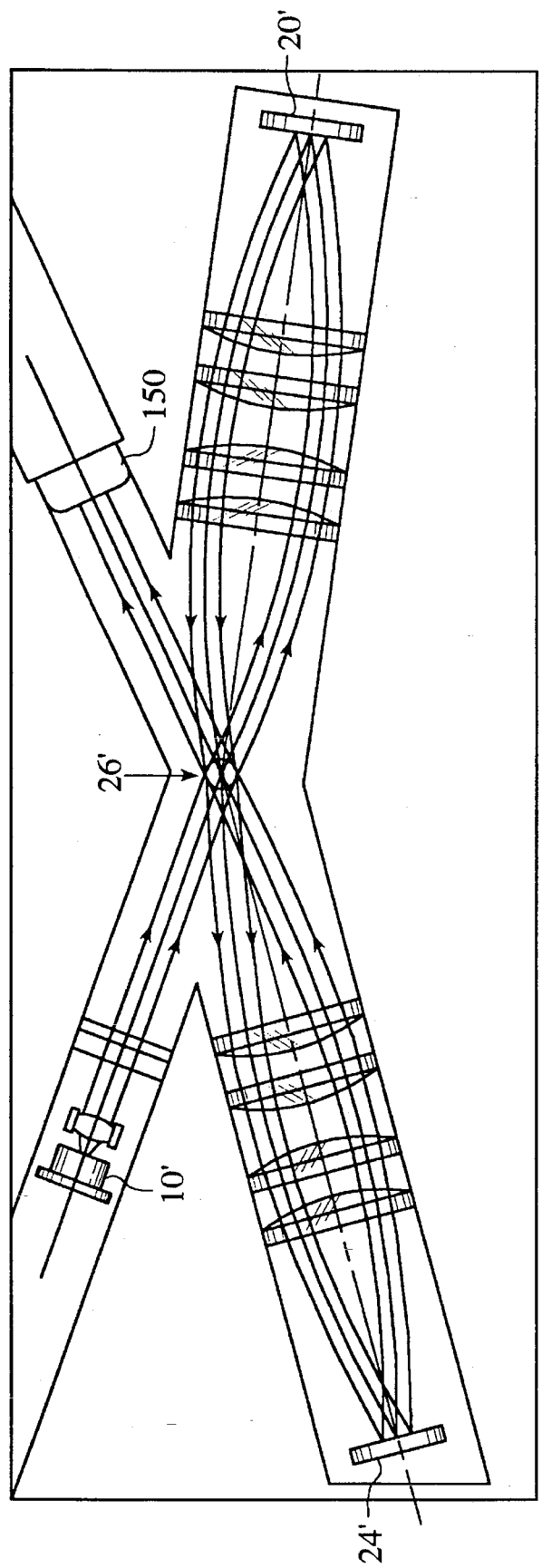
FIG. 2a is a top view of an alternate embodiment of the present invention.

FIG. 2 is similar to FIG. 1, except that a detector 150 is placed at a forward angle relative to laser 10. The angle of offset, $\delta$, is in the range of 90°–150°. FIG. 2 lacks the light collection system 300 of FIG. 1, including condensers 28. Spherical reflector 27 is also absent. Detector 150 takes advantage of the multiple reflections of the beam in the following way. Since the detector is monitoring the central portion of the view volume, 26, it is essentially sampling light from the most intense beam region. However, this light is decreased due to scattering of light by particles. In fact, each time the beam passes a particle, the intensity of the beam is reduced by the amount of light scattered by the particle. In a sense, the detector 150 is an extinction type sensor because the amount of light decrease is due to attenuation of the beam or extinction of a portion of the beam by a particle. The amount of energy attenuated from the beam is related to the number of passes multiplied by the amount of light scattered from a particle. The multiple reflections of the beam between the slightly misaligned optical elements 20 and 24 will result in a larger light loss signal than would occur without a large number of passes between the reflective elements.

From this embodiment, it is seen that the re-entrant light system of the present invention operates with either a direct observation of scattering which is intensified by multiple light passes or by observation of a diminution or attenuation and beam intensity from obscuration caused by particles in the beam path. On the other hand, the embodiment of FIG. 1 measures increases in the optical signal as light is directed toward the detector through light collection optics in a manner such that a particle resembles a small source of light. In fact, light is being scattered over a range of angles, but collection of light over the range provides an enhanced signal so that particles down to 0.1 microns register a signal. Generally, the size of a particle is proportional to the signal which is registered at the detector in the apparatus of FIG. 1. Conversely, the amount of obscuration of the detected beam in FIG. 2 is proportional to the size and quantity of particles.

Figure 3:
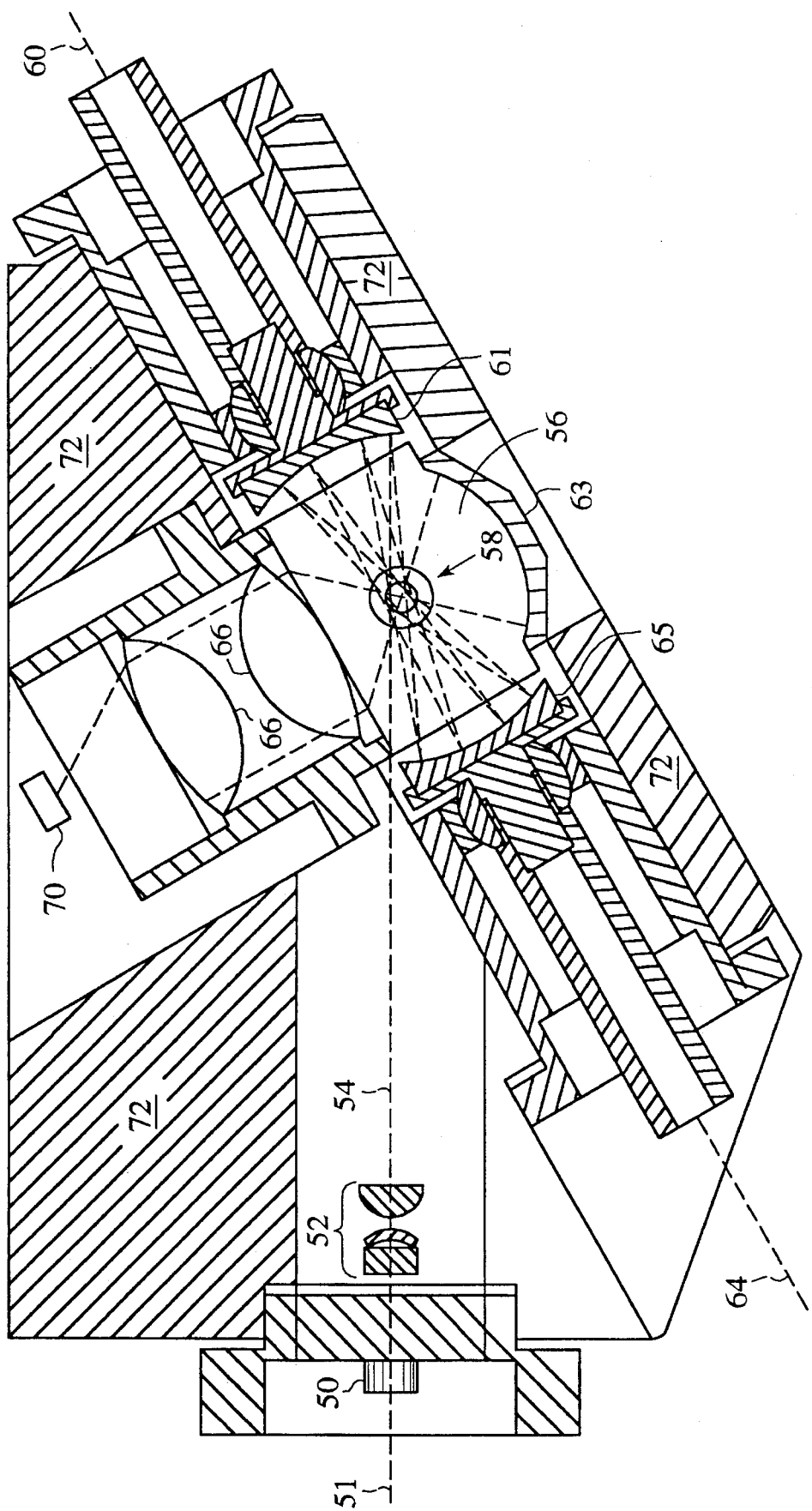
FIG. 3 is a top view of another alternate embodiment of the present invention.

Referring now to FIG. 3, another embodiment of the present invention is shown. In this case, the two mirrored surfaces are concave spherical reflectors residing on slightly misaligned optical axes and having slightly different alignment of their centers of curvatures. Laser 50 emits a beam which is shaped by illumination optics 52 to produce a laser beam 54 of a desired shape. Beam 54 is projected along laser optical axis 51, enters optical cavity 56, passes through view volume 58 and reaches the first concave spherical reflector 61 residing on optical axis 60. Optical axis 60 is defined as the axis of symmetry of reflector 61.

Reflector 61 focuses beam 54 into view volume 58. Beam 54 then diverges and is reflected off the second concave spherical reflector 65. Reflector 65 resides on optical axis 64 defined as the axis of symmetry of reflector 65. However, since optical axes 60 and 64 of the two spherical reflectors 61 and 65 are slightly misaligned such that they are not coincident or parallel, beam 54 is not focused to the same point within view volume 58 but, rather, slightly beside itself. A misalignment as small as 1–2 degrees will result in beam 54 being repeatedly focused to a slightly different position within view volume 58. Beam 54 continues to be reflected between reflectors 61 and 65 each time being focused to a point within view volume 58 eventually filling it with overlapping focal points. Additionally, as in the previous embodiment, since beam 54 is focused to a slightly different position after each reflection, the size of view volume 58 is enlarged. As a result, a larger area is available for the introduction of a sample flow of fluid. Beam 54 will continue to be reflected between the two reflectors 61 and 65 until it falls off the edge of either reflector 61 or 65.

The size of reflectors 61 and 65 is dictated by certain parameters. Reflector 61 must be large enough such that one of its edges extends into the path of laser beam 54 to allow for reflection of beam 54 back towards view volume 58. Reflector 65 must not be so large that its edges extend into the path of laser beam 54 along laser optical axis 51. Light which eventually falls off the edge of reflectors 61 or 65 is received by light traps 72 surrounding optical cavity 56.

Fluid, which may be a gas or liquid, is then passed through view volume 58. As the fluid flows through view volume 58, light scattered by mobile particles is directed by collection optics 66 towards detector 70. Light which is originally scattered away from detector 70 may be directed back towards detector 70 by an additional spherical reflector 63 which is located directly across from detector 70 on the opposite side of optical cavity 56.

Figure 4:
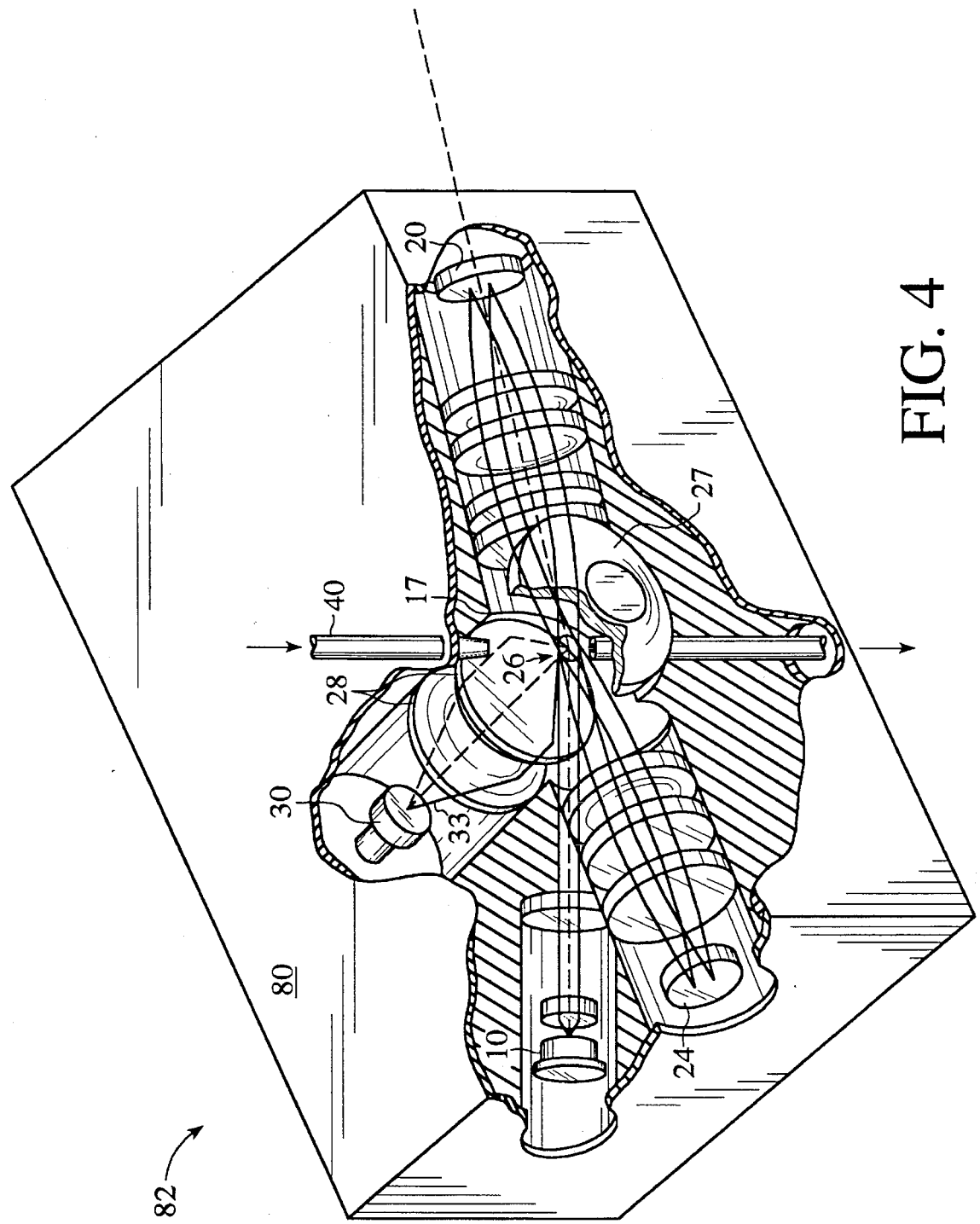
FIG. 4 is a perspective view of the apparatus of FIG. 1.

Referring now to FIG. 4, a perspective-illustration of the present detection invention of FIG. 1 is shown. Fluid is introduced into view volume 26 by means of nozzle 40 at a rate up to and exceeding 1 cfm in the case of gas. Nozzle 40 is aligned such that the fluid that is to be tested is directed through the entire area of view volume 26. The previously mentioned first, second, third and fourth axes all lie within small angles of a horizontal plane typified by the horizontal surface 80 of housing 82. This allows all components of the apparatus to fit in a box-like housing, except that nozzle 40 is perpendicular to surface 80. This allows a plurality of similar housings to be placed side-by-side to provide an extended view volume consisting of multiple particle sensing cavities. Such multiple cavities will accommodate higher flow rates than a single cavity and may include a light source that is removable mounted thereto.

In cases where liquids are used, seals at edges of the lenses must be provided relative to the housing for confining the liquid to the central cavity. Closed cells, rectangular cells or other cell geometries may be used.

We claim:

1. Apparatus for optically detecting particles in a fluid comprising:

first means for reflecting light having a first optical axis, second means for reflecting light having a second optical axis, the first and second reflective means being spaced apart and defining an optical cavity therebetween, light source means for projecting a beam along a third optical axis from outside said optical cavity to the inside thereof, said first, second and third optical axes intersecting in a view volume, with said first optical axis being displaced from said third optical axis, defining an angle α and said second optical axis being displaced from said third optical axis, defining an angle β with a difference between α and β being greater than 0°, means for introducing a fluid flow into said optical cavity, a portion of said flow traversing said view volume whereby particles in said flow scatter light, and light collection and detector means having a fourth optical axis intersecting said view volume for sensing light from said view volume.

2. The apparatus of claim 1 wherein said first and second light reflecting means repeatedly reflect said projected beam through said view volume, such that said light beam overlaps itself within said view volume increasing the light intensity therein.

3. The apparatus of claim 1 wherein said first and second means for reflecting light are concave spherical reflectors.

4. The apparatus of claim 3 wherein said concave spherical reflectors repeatedly focus said beam into said view volume, such that the focal spots overlap increasing the light intensity therein.

5. The apparatus of claim 1 wherein said first and second means for reflecting light comprise light refractors in focal relation with flat or spherical reflectors.

6. The apparatus of claim 5 wherein said light refractors associated with the first means for reflecting light have an edge proximate to the beam.

7. The apparatus of claim 1 wherein said light collection and detector means has an axis offset from the first or second optical axis means by less than 20°.

8. The apparatus of claim 1 wherein said light collection and detector means has an axis within 20° of perpendicularity of each of the first and second axes.

9. A particle detector as in claim 1 wherein said light collection and detector means comprises a light detector and a reflector situated at said optical cavity but having an optical axis to reflect said scattered light towards said detector, said detector and reflector defining an axis within 20° of perpendicularity of each of the first and second axes.

10. A particle detector as in claim 1 wherein said detecting means has a light collector disposed between the optical cavity and the detector means.

11. The apparatus of claim 1 wherein said optical cavity is enclosed by a housing within said light source means removably attached thereto.

12. An improved method for optically detecting particles in fluid comprising the steps of:

arranging a first reflector along a first optical axis, arranging a second reflector along a second optical axis such that said first and second reflectors are spaced apart and define an optical cavity therebetween, said axis of first and second reflectors being slightly misaligned, projecting a light beam along a third optical axis from outside of said optical cavity to the inside thereof, said first, second and third axis intersecting in a view volume, the light beam being multiply reflected between the first and second reflectors, the multiple reflections traversing the view volume, introducing a fluid flow into said optical cavity such that a portion of said flow traverses said view volume wherein particles in said flow scatter light, sensing said scattered light wherein said sensor is a light collection means and a detector arranged on a fourth optical axis for viewing said view volume.

13. The method of claim 12 wherein said first and second reflectors repeatedly focus said beam into said view volume such that the focal spots overlap increasing the light intensity therein.

14. The method of claim 12 wherein said light beam is shaped by lenses such that it has a predetermined shape.

15. The method of claim 12 further defined by sensing scattered light by measuring attenuation of light in the optical cavity.

16. The method of claim 12 further defined by sensing scattered light by measuring an increase of light in the optical cavity.

17. An improved device for optically detecting particles in a fluid comprising:

a first reflector having a first optical axis, a second reflector having a second optical axis, said first and second reflectors being spaced apart and defining an optical cavity therebetween, said axis of said first and second reflectors slightly misaligned, a light source for projecting a beam along a third optical axis from outside said optical cavity to the inside thereof, said first, second and third optical axes intersecting in a view volume, said first reflector having an edge extending across said third optical axis, for intercepting and reflecting said beam back towards said second reflector, means for introducing a fluid flow into said optical cavity, a portion of said fluid flow traversing said view volume whereby particles in said flow scatter light, a detector means having a fourth optical axis intersecting said view volume for sensing scattered light inside view volume.

18. The device of claim 17 wherein said first and second reflectors repeatedly reflect said projected beam through said view volume such that said light beam overlaps itself within said view volume increasing the light intensity therein.

* * * * *